US012527386B2

(12) United States Patent
Fortuna Cohen

(10) Patent No.: US 12,527,386 B2
(45) Date of Patent: Jan. 20, 2026

(54) WAX APPLICATOR

(71) Applicant: Mali Fortuna Cohen, Tlamim (IL)

(72) Inventor: Mali Fortuna Cohen, Tlamim (IL)

( * ) Notice: Subject to any disclaimer, the term of this patent is extended or adjusted under 35 U.S.C. 154(b) by 252 days.

(21) Appl. No.: 18/281,585

(22) PCT Filed: Mar. 14, 2022

(86) PCT No.: PCT/IL2022/050286
§ 371 (c)(1),
(2) Date: Sep. 12, 2023

(87) PCT Pub. No.: WO2022/195583
PCT Pub. Date: Sep. 22, 2022

(65) Prior Publication Data

US 2024/0138540 A1 May 2, 2024

Related U.S. Application Data

(60) Provisional application No. 63/160,971, filed on Mar. 15, 2021.

(51) Int. Cl.
*A45D 26/00* (2006.01)
*A61K 8/92* (2006.01)
*A61Q 9/04* (2006.01)

(52) U.S. Cl.
CPC ............ *A45D 26/0014* (2013.01); *A61K 8/92* (2013.01); *A61Q 9/04* (2013.01)

(58) Field of Classification Search
CPC ...... A45D 26/0014; A61Q 9/04; H02J 7/0044
See application file for complete search history.

(56) References Cited

U.S. PATENT DOCUMENTS 5,681,388 A 10/1997 Legrain et al.
5,816,726 A 10/1998 Debourg et al.
6,039,482 A * 3/2000 Smal ................. A45D 26/0014 401/131
2004/0037608 A1 2/2004 Cochran
2004/0258459 A1 12/2004 Esmoris
2009/0087247 A1 4/2009 Jennings et al.
2019/0387862 A1 12/2019 Duarte De Baez et al.
2019/0387870 A1 12/2019 Goldfarb
2021/0298447 A1 * 9/2021 Fan .................... A45D 26/0014

FOREIGN PATENT DOCUMENTS

CN 111345571 A 6/2020
FR 1459825 A 6/1966
GB 2334014 A 8/1999
GB 2411340 A 8/2005

* cited by examiner

*Primary Examiner* — Todd J Scherbel

(57) ABSTRACT

The present subject matter provides a wax applicator configured to apply heated wax onto a skin of a patient for hair removal, the wax applicator comprising: a wax chamber having at least one opening; a heating element attached to the wax chamber, configured to heat the wax in the wax chamber, thus giving rise to melted wax; and a pushing element configured to push the melted wax out of the wax chamber through at least one of the at least one opening, wherein at least one component of the wax applicator is electrically operated, and the at least one electrically operated component is electrically connected to at least one electrical power supply. Additional embodiments of the wax applicator, and a method of applying heated wax onto a skin of a patient for hair removal with the wax applicator, are disclosed herein as well.

19 Claims, 6 Drawing Sheets

WAX APPLICATOR

CROSS-REFERENCE TO RELATED APPLICATION

This application is a continuation in part application of PCT application No. PCT/IL2022/050286. This application claims priority to U.S. Provisional Patent Application No. 63/160,971, filed Mar. 15, 2021, the entire contents of which is incorporated herein by reference in its entirety.

FIELD

The present subject matter relates to hair removal. More particularly, the present subject matter relates to waxing for hair removal.

BACKGROUND

Hair removal is a process of deliberate removal of body hair. One of the ways to remove body hair is by waxing. Waxing is a process of hair removal from the root by using a covering of a sticky substance, for example wax, to adhere to body hair, and then removing this covering and thereby pulling out the hair from the follicle. Almost any area of the boy can be waxed, including eyebrows, face, pubic hair, legs, arms, back, abdomen, knuckles, and feet. There are two types of waxing: strip waxing; and stripless waxing.

In strip waxing soft wax is spread thinly over the skin. A cloth or paper strip is applied and pressed firmly, adhering the strip to the wax and the wax to the skin. The strip is then quickly ripped against the direction of hair growth, as parallel as possible to the skin to avoid trauma of the skin. This removes the wax along with hair. One form of strip waxing involves spreading of heated wax over the skin.

In stripless waxing, heated wax is applied thickly on the skin with no cloth or paper strips. The wax then hardens when the wax cools, thus allowing easy removal of hair without the aid of cloths or strips. Stripless waxing is very beneficial to people who have sensitive skin. Stripless wax does not adhere to the skin as much as strip wax does, thus making it a good option for sensitive skin as finer hairs are more easily removed because the hard wax encapsulates the hair as it hardens. The stripless waxing method can also be less painful.

SUMMARY

Unless otherwise defined, all technical and scientific terms used herein have the same meaning as commonly understood by one of ordinary skill in the art to which this subject matter belongs. Although methods and materials similar or equivalent to those described herein can be used in the practice or testing of the present subject matter, suitable methods and materials are described below. In case of conflict, the patent specification, including definitions, will control. In addition, the materials, methods, and examples are illustrative only and not intended to be limiting.

According to one aspect of the present subject matter, there is provided a wax applicator configured to apply heated wax onto a skin of a patient for hair removal, the wax applicator comprising:

a wax chamber having at least one opening;

a heating element attached to the wax chamber, configured to heat the wax in the wax chamber, thus giving rise to melted wax; and a pushing element configured to push the melted wax out of the wax chamber through at least one of the at least one opening, wherein at least one component of the wax applicator is electrically operated, and the at least one electrically operated component is electrically connected to at least one electrical power supply.

According to one embodiment, the electrical power supply is electricity mains, and the wax applicator further comprising an electrical socket electrically connected to the at least one electrically operated component, and is configured to electrically connect to the electricity mains.

According to another embodiment, the electrical power supply is an electrical power source, and the wax applicator further comprising at least one electrical power source electrically connected to the at least one electrically operated component.

According to yet another embodiment, the at least one electrical power source is a rechargeable power source, and the rechargeable power source is electrically connected to the electrical socket.

According to still another embodiment, the heating element is an electrical heating element.

According to a further embodiment, the heating element is configured to heat the wax that is in the wax chamber to a temperature of at least substantially 40° C.

According to yet a further embodiment, the wax applicator further comprising a thermostat and a temperature sensor configured to sense a temperature of wax in the wax chamber, wherein the thermostat is electrically connected to the heating element, and the temperature sensor is signally connected to the thermostat, wherein the temperature sensor is configured to sense the temperature of the wax that is in the wax chamber and transmit a signal indicative of the sensed temperature to the thermostat, and wherein the thermostat is configured to compare between the sensed temperature and a predetermined threshold temperature and accordingly switch-on or switch-off the heating element.

According to still a further embodiment, the wax applicator further comprising an on-off switch electrically connected between the electrical power supply and the at least one electrically operated component.

According to an additional embodiment, the wax applicator further comprising at least one temperature setting switch electrically connected to the thermostat and configured to allow determination of the threshold temperature.

According to yet an additional embodiment, the wax applicator further comprising at least one display configured to display parameters indicative of the operation of the wax applicator.

According to still an additional embodiment, the pushing element is a piston-like pushing element configured to be pushed inside the wax chamber, thereby push melted wax from the wax chamber through the at least one opening.

According to another embodiment, the pushing element is manually actuated.

According to yet another embodiment, the wax applicator further comprising an electrical motor mechanically attached to the pushing element, and configured to actuate the pushing element.

According to still another embodiment, the wax applicator further comprising a screwed shaft positioned between the motor and the pushing element, wherein the he motor is configured to turn the screwed shaft in two directions—clockwise and counterclockwise, wherein when he screwed shaft is turned in one direction the screwed shaft is pushed forward and thereby push the pushing element in the wax chamber toward an opening that allows exit of melted wax from the wax chamber, and wherein when the screwed shaft is turned in an opposite direction the screwed shaft is pulled backward and thereby pull the pushing element in the wax chamber away from the opening that allows exit of melted wax from the wax chamber.

According to a further embodiment, the wax applicator further comprising at least one direction switch configured to control the direction of the turning of the motor, thereby controlling the direction of movement of the pushing element.

According to yet a further embodiment, the wax applicator further comprising at least one speed switch configured to control a speed of turning of the motor, thereby control a speed of movement of the pushing element.

According to still a further embodiment, the wax applicator further comprising at least one wax application head configured to attach to an opening that allows exit of melted wax from the wax chamber, and allow passage of the melted wax through the wax application head.

According to an additional embodiment, the wax application head is hollow, and comprising an attachment portion at one side of the wax application head, configured to attach to the opening that allows exit of melted wax from the wax chamber, and a nozzle at an opposite side of the wax application head, configured to allow application of a controlled amount of the melted wax on the skin of the patient.

According to yet an additional embodiment, the wax applicator comprising a set of multiple wax application heads, wherein the attachment portion is similar in all the wax application heads, and the size and shape of the nozzle is different in each wax application head.

According to still an additional embodiment, the wax applicator further comprising a body configured to enclose internal components of the wax applicator, and carry on an external surface of the body external components of the wax applicator.

According to another embodiment, the body comprising a first body part and a second body part that are configured to attach one to the other and enclose the internal parts of the wax applicator, while the external surface of at least one of the first body part and the second body part is configured to carry the external components of the wax applicator.

According to yet another embodiment, the wax applicator further comprising a stand configured to hold the wax applicator, wherein the stand comprising:

- a base configured to stand on or attach to a surface; and
- a holding element attached to the base and configured to hold the wax applicator.

According to still another embodiment, the base is configured to stand on a horizontal surface.

According to a further embodiment, the base is configured to attach to a diagonal or vertical surface.

According to yet a further embodiment, the stand is configured to hold the wax applicator in a manner that the opening that allows exit of melted wax from the wax chamber faces downwards.

According to still a further embodiment, the stand is configured to diagonally hold the applicator, an angle relative to the surface.

According to an additional embodiment, the stand is a charging stand that is configured to electrically charge a rechargeable power source of the wax applicator.

According to another aspect of the present subject matter, there is provided a method of applying heated wax onto a skin of a patient for hair removal, the method comprising:

- providing the wax applicator configured to apply heated wax onto a skin of a patient for hair removal, the wax applicator comprising:
  - a wax chamber having at least one opening;
  - a heating element attached to the wax chamber, configured to heat the wax in the wax chamber, thus giving rise to melted wax; and
  - a pushing element configured to push the melted wax out of the wax chamber through at least one of the at least one opening,
- wherein at least one component of the wax applicator is electrically operated, and the at least one electrically operated component is electrically connected to at least one electrical power supply;
- filling the wax chamber with wax;
- melting the wax by heating; and
- pushing the melted wax out from the wax chamber while applying the melted wax on the skin of the patient.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings.

DESCRIPTION OF THE PREFERRED EMBODIMENTS

Figure 1A:
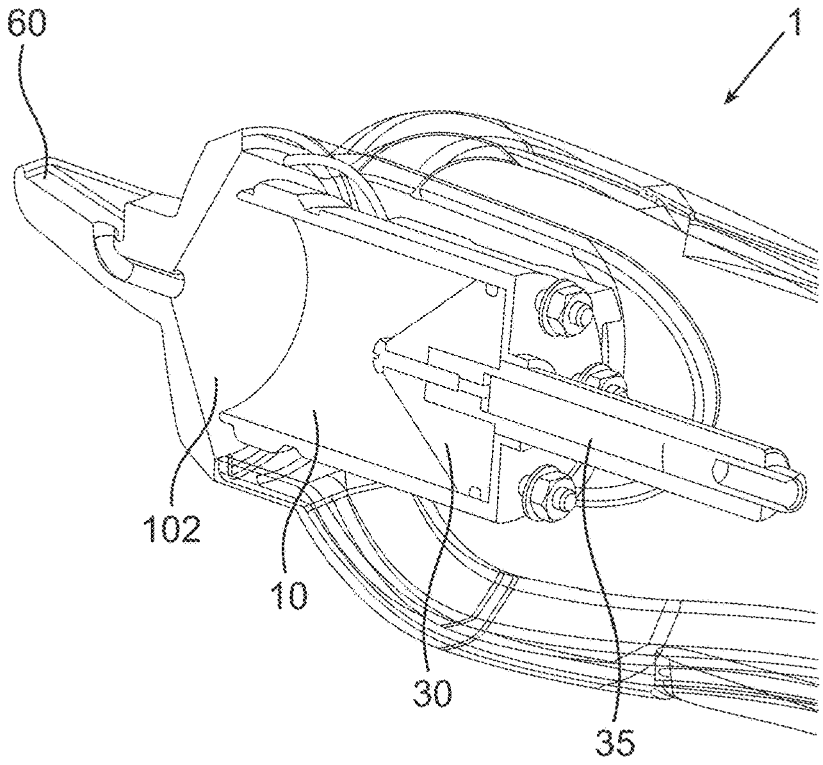
FIGS. 1A-B schematically illustrate, according to an exemplary embodiment, perspective partial views of a wax applicator, showing two states of a pushing element.

Before explaining at least one embodiment in detail, it is to be understood that the subject matter is not limited in its application to the details of construction and the arrangement of the components set forth in the following description or illustrated in the drawings. The subject matter is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale.

For clarity, non-essential elements were omitted from some of the drawings.

The present subject matter provides a wax applicator configured to apply heated wax onto a skin of a patient for hair removal, the wax applicator comprising:

a wax chamber having at least one opening;

a heating element attached to the wax chamber, configured to heat the wax in the wax chamber, thus giving rise to melted wax; and a pushing element configured to push the melted wax out of the wax chamber through at least one of the at least one opening.

The present subject matter further provides a method of applying heated wax onto a skin of a patient for hair removal, the method comprising:

providing a wax applicator configured to apply heated wax onto a skin of a patient for hair removal, the wax applicator comprising:

a wax chamber having at least one opening;

a heating element attached to the wax chamber, configured to heat the wax in the wax chamber, thus giving rise to melted wax; and a pushing element configured to push the melted wax out of the wax chamber through at least one of the at least one opening;

filling a wax chamber of the wax applicator with wax;

melting the wax by heating; and pushing the melted wax out from the wax chamber while applying the melted wax on the skin of the patient.

Figure 1B:
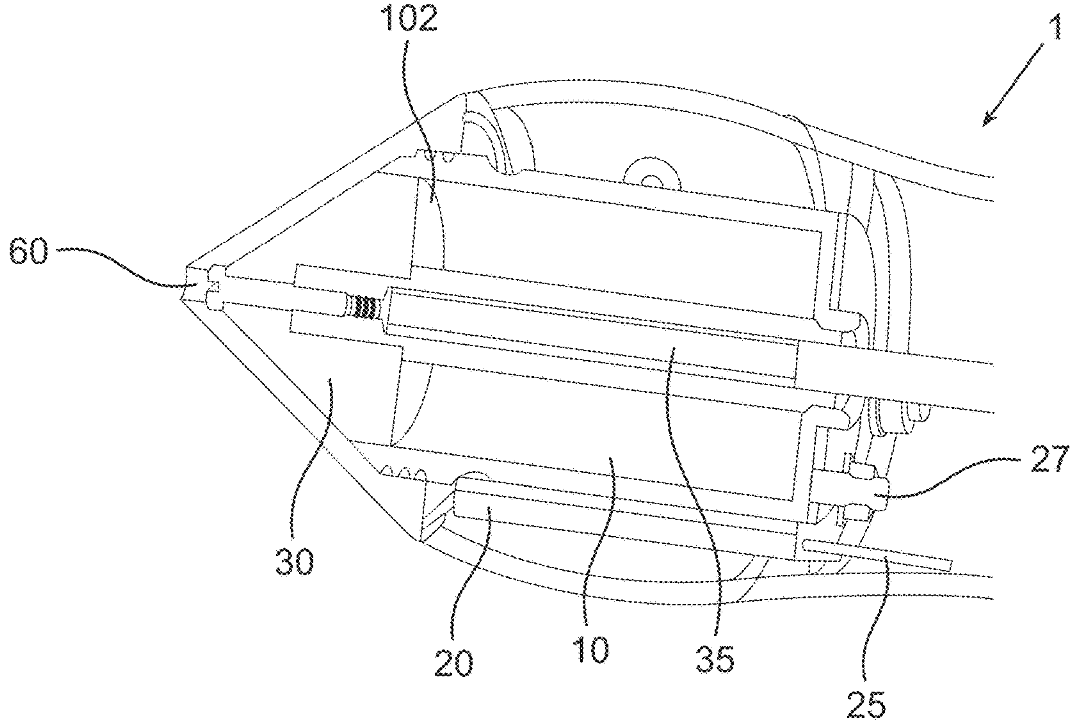

Referring now to FIGS. 1A-B schematically illustrating, according to an exemplary embodiment, perspective partial views of a wax applicator, showing two states of a pushing element. FIGS. 1A-B show various embodiments of the components of the wax applicator.

As can be seen for example in FIG. 1B, The wax applicator 1 comprises: a wax chamber 10 having at least one opening 102; a heating element 20 attached to the wax chamber 10, configured to heat the wax in the wax chamber 10, thus giving rise to melted wax; and a pushing element 30 configured to push the melted wax out of the wax chamber 10 through at least one of the at least one opening 102.

According to one embodiment, shown in FIGS. 1A-B, the wax chamber 10 comprises one opening 102. The opening 102 allows insertion of wax into the wax chamber 10, and exit of melted wax from the wax chamber 10. According to another embodiment, the wax chamber 10 comprises multiple openings 102, for example two openings 102—a first opening and a second opening. For example, the first opening is configured to allow insertion of wax into the wax chamber 10, and the second opening is configured to allow exit of melted wax from the wax chamber 10. According to some other embodiments, the wax chamber 10 comprises at least one opening 102 that is configured to allow insertion of wax into the wax chamber, and at least one opening 102 that is configured to allow exit of melted wax from the wax chamber 10. Thus, as mentioned above, overall, the wax chamber 10 comprises at least one opening 102.

According to one embodiment, the wax chamber 10 is configured to accommodate any type of wax, particularly wax that is used for hair removal—solid wax in any size and shape, for example wax bars, wax flakes, and the like; or wax in a paste-like texture, for example partially melted wax; or liquid wax, for example fully melted wax. The partially melted wax and the fully melted wax are obtained by heating solid wax.

The heating element 20 that is attached to the wax chamber 10 is configured to heat the wax that is in the wax chamber 10, thus giving rise to melted wax. Any type of heating element 20 is under the scope of the present subject matter. The heating element 20 is configured to heat the wax, and thereby melt the wax, namely cause the wax to be in a paste-like texture, or in liquid form. Since the melting temperature of most types of wax is substantially 40° C., or above, the heating element 20 is configured to heat the wax that is in the wax chamber 10 to a temperature of at least substantially 40° C.

According to one embodiment, the wax chamber 10 is configured to keep melted wax inside the wax chamber 10 in a melted state for an extended period of time, also without needing to heat the melted wax. In other words, the wax chamber 10 is configured to keep high temperatures inside it for an extended period of time, for example substantially 10-15 minutes. This can be achieved, for example, by an embodiment according to which the wax chamber 10 is made of a heat insulating material. Another embodiment, is that the wax chamber 10 is closed, and therefore loss of heat from inside the wax chamber 10 is greatly eliminated. This feature of the wax chamber 10 allows saving energy, since there is no need to operate the heating element 20 constantly in order to keep the wax in the wax chamber 10 in a melted state.

Figure 2:
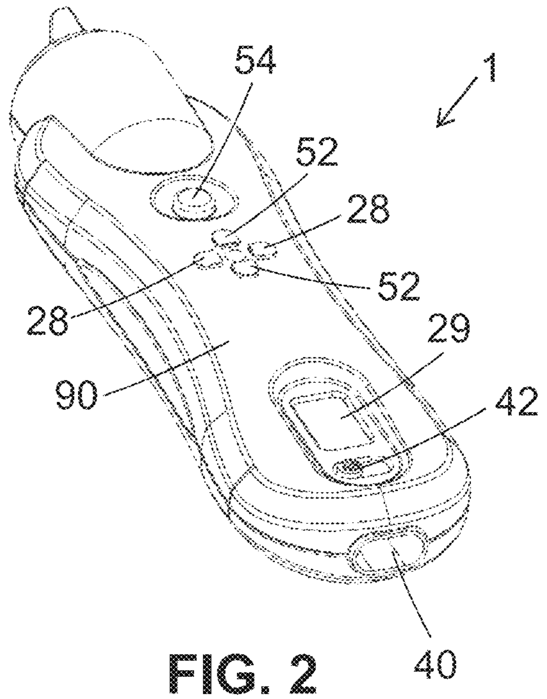
FIG. 2 schematically illustrates, according to an exemplary embodiment, a back perspective view of a wax applicator.

Referring now to FIG. 2, schematically illustrating, according to an exemplary embodiment, a back perspective view of a wax applicator. FIG. 2 shows external components of the wax applicator 1.

According to one embodiment, at least one component of the wax applicator 1 is electrically operated, and the at least one electrically operated component is electrically connected to at least one electrical power supply. Any type of electrical power supply is under the scope of the present subject matter, for example, mains electricity, an electrical power source, like any type of electrical battery such as a disposable battery, a rechargeable battery, and the like.

According to one embodiment, the electrical power supply is the mains electricity, and the wax applicator 1 is configured to electrically connect to the electricity mains, for example with an electrical cord and plug. Thus, as shown in FIG. 2, according to another embodiment, the wax applicator 1 further comprises an electrical socket 40 electrically connected to the at least one electrically operated component of the wax applicator 1, and is configured to electrically connect to the electricity mains, for example with a cord and plug.

According to another embodiment, the electrical power supply is an electrical power source 45, shown in FIGS. 4B-C, hereinafter. Thus, according to this embodiment, the wax applicator 1 further comprises at least one electrical power source 45 electrically connected to the at least one electrically operated component of the wax applicator 1. According to yet another embodiment, when the electrical power source 45 is rechargeable, like a rechargeable battery 45, the rechargeable power source 45 is electrically connected to the electrical socket 40.

According to one embodiment, the heating element 20 is an electrical heating element 20. Thus, according to this embodiment, the heating element 20 is electrically connected to an electrical power supply. When the electrical power supply is the electricity mains, the electrical heating element 20 is electrically connected to the electrical socket 40; and when the electrical power supply is an electrical power source 45, the electrical heating element 20 is electrically connected to the electrical power source 45.

Returning now to FIG. 1B. According to one embodiment, the wax applicator 1 further comprises a thermostat 25 and a temperature sensor 27 configured to sense a temperature of wax in the wax chamber 10, wherein the thermostat

25 is electrically connected to the heating element 20, and the temperature sensor 27 is signally connected to the thermostat 25. The temperature sensor 27 is configured to sense the temperature of the wax that is in the wax chamber 10 and transmit a signal indicative of the sensed temperature to the thermostat 25. The thermostat 25, in its turn, is configured to compare between the sensed temperature and a predetermined threshold temperature and accordingly switch-on or switch-off the heating element 20. When the sensed temperature is lower than the threshold temperature, the thermostat 25 is configured to allow operation of the heating element 20, or switch-on the heating element 20. When the sensed temperature is higher than the threshold temperature, the thermostat 25 is configured to switch-off the heating element 20. Thus, this embodiment ensures that the wax that is in the wax chamber 10 is kept at a predetermined threshold temperature, and that the temperature of the wax in the wax chamber 10 does not raise above the threshold temperature.

Returning now to FIG. 2. According to one embodiment, the wax applicator 1 further comprises an on-off switch 42 electrically connected between the electrical power supply and the at least one electrically operated component. When the electrical power supply is the electricity mains, the on-off switch 42 is electrically connected between the electrical socket 40 and the at least one electrically operated component of the wax applicator 1. Alternatively, when the electrical power supply is the at least on electrical power source 45, the on-off switch 42 is electrically connected between the at least one electrical power source 45 and the at least one electrically operated component of the wax applicator 1. The on-off switch 42 is configured to allow switching-on and switching-off operation of components of the wax applicator 1, for example operation of the heating element 20, or operation of other components that will be described hereinafter.

Still remaining in FIG. 2, according to one embodiment, the wax applicator 1 further comprises at least one temperature setting switch 28 electrically connected to the thermostat 25 and configured to allow determination of the threshold temperature. For example, as can be seen in FIG. 2, the wax applicator 1 comprises two temperature setting switches 28, one temperature setting switch 28 for increasing the threshold temperature, and another temperature setting switch 28 for decreasing the threshold temperature. It should be mentioned, though, that this embodiment is only exemplary. Any type of mechanism for determining the threshold temperature is under the scope of the present subject matter.

Still remaining in FIG. 2, according to one embodiment, the wax applicator 1 further comprises at least one display 29. The display 29 is configured to display parameters indicative of the operation of the wax applicator 1. For example, the display 29 is configured to indicate whether the heating element 20 is on or off, indicate the predetermined threshold temperature, indicate the sensed temperature of the wax in the wax chamber 10, indicate status of the electrical power source 45—for example a level of charging of the rechargeable power source 45, indication whether there is a need to replace or charge the electrical power source 45, and the like. Additional parameters that can be displayed in the display 29 will be described hereinafter.

The pushing element 30 is configured to push melted wax that is in the wax chamber 10, and force exit of the melted wax through the at least one opening 102 as described above. Any type of pushing element 30 is under the scope of the present subject matter. For example, according to one embodiment, the pushing element 30 is a kind of piston. Thus, the piston-like pushing element 30 is configured to be pushed inside the wax chamber 10, thereby push melted wax from the wax chamber 10 through the at least one opening 102.

According to one embodiment, the pushing element 30 is manually actuated. Thus, according to this embodiment, the wax applicator 1 further comprises a manual actuator for manually actuating the pushing element 30, for example in a form of a trigger that is mechanically attached to the pushing element 30. Manually pressing the trigger causes movement of the pushing element 30 inside the wax chamber 10. Alternatively, the manual actuator can be in a form of an outer knob that is attached to the pushing element 30, and configured to be manually pushed, thereby causing movement of the pushing element 30 inside the wax chamber 10. It should be noted that the aforementioned embodiments are only exemplary embodiments of the manual activator, and they should not be considered as limiting the scope of the present subject matter.

Figure 4A:
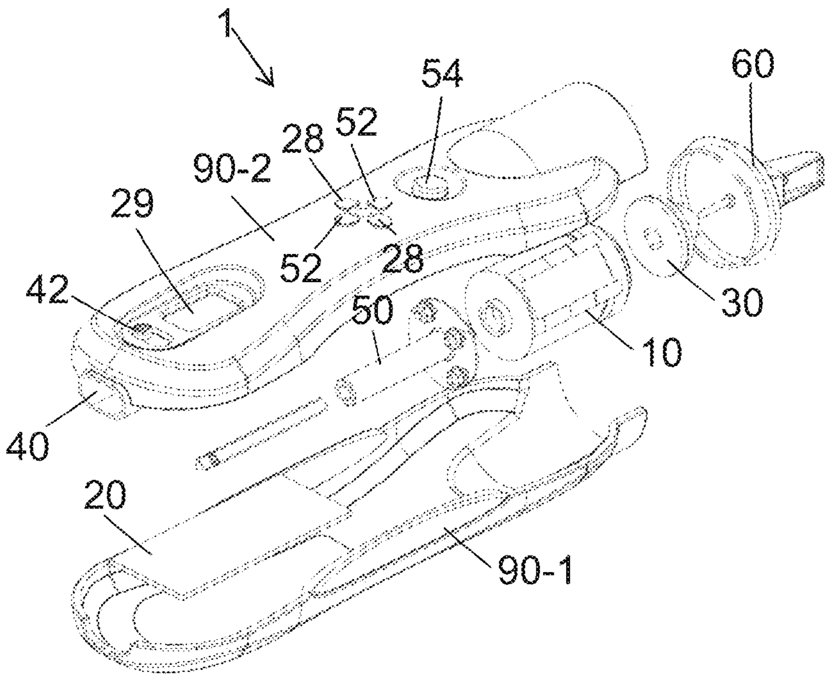
FIGS. 4A-C schematically illustrate, according to an exemplary embodiment, various different aspects of an exploded view of a wax applicator.

According to another embodiment, the wax applicator 1 further comprises a motor 50 mechanically attached to the pushing element 30, and configured to actuate the pushing element 30. Any mechanism for actuating the movement of the pushing element 30 by the motor 50 is under the scope of the present subject matter. The motor is shown in FIGS. 4A-C, hereinafter, and an exemplary embodiment of the mechanism of actuation of the pushing element 30 by the motor is illustrated in FIGS. 1A-B.

Returning now to FIGS. 1A-B. FIGS. 1A-B schematically illustrate two states of the pushing element 30, optionally actuated by a motor. FIGS. 1A-B show a pushing element 30 in a form of a piston. In FIG. 1A, the pushing element 30 is in a fully pulled position, mostly distant from an opening 102 that allows exit of melted wax from the wax chamber 10. In FIG. 1B, the pushing element 30 is in a fully pushed position, mostly adjacent to the opening 102 that allow exit of melted wax from the wax chamber 10. Thus, the pushing element 30 is configured to be pushed and pulled between these two positions, either manually, or with a motor 50, as mentioned above.

An exemplary mechanism for pushing and pulling the pushing element 30 by the motor 50 is described in the following embodiment. The motor 50 is shown in FIGS. 4A-C hereinafter. According to one embodiment, seen in FIGS. 1A-B, the wax applicator 1 further comprises a screwed shaft 35 positioned between the motor 50 and the pushing element 30. The motor 50 is configured to turn the screwed shaft 35 in two directions—clockwise and counterclockwise. When he screwed shaft 35 is turned in one direction, for example clockwise, the screwed shaft 35 is pushed forward and thereby push the pushing element 30 in the wax chamber 10 toward an opening 102 that allows exit of melted wax from the wax chamber 10, as seen in FIG. 1B. This, in turn, causes exit of melted wax from the wax chamber 10 through the opening 102 that allows exit of meted wax. On the other hand, when the screwed shaft 35 is turned in an opposite direction, for example counterclockwise, the screwed shaft 35 is pulled backward and thereby pull the pushing element 30 in the wax chamber 10 away from the opening 102 that allows exit of melted wax from the wax chamber 10, as seen in FIG. 1A. This position of the pushing element 30, shown in FIG. 1A, allows insertion of wax into the wax chamber 10. It should be noted, though, that this mechanism for actuating the pushing element 30 by the motor 50 is only exemplary, and should not be considered as limiting the scope of the present subject matter.

According to one embodiment, the motor 50 is an electrical motor 50. Thus, similarly to the heating element 20, the motor 50 is electrically connected to the mains electricity, for example through the electrical socket 40, shown for example in FIG. 2, and/or to the electrical power source 45, shown for example in FIG. 4C. According to another embodiment, the wax applicator 1 further comprises at least one direction switch 52 configured to control the direction of the turning of the motor 50, thereby controlling the direction of movement of the pushing element 30, as shown in FIG. 2. According to yet another embodiment, the wax applicator 1 comprises two direction switches—one direction switch 52, when actuated by a user, prompts operation of the motor 50 in a manner that pushes the pushing element 30 forward, thus causing exit of melted wax from the wax chamber 10; and another direction switch 52, when actuated by a user, prompts operation of the motor 50 in a manner the pulls the pushing element 30 away from the opening 102 that allow exit of melted wax from the wax chamber 10. In another embodiment, the display 29 is configured to display the direction of movement of the pushing element 30.

According to a further embodiment, the wax applicator 1 further comprises at least one speed switch 54, also shown in FIG. 2. The speed switch 54 is configured to control the speed of turning of the motor 50, thereby control the speed of movement of the pushing element 30. According to yet a further embodiment, the display 29 is additionally configured to display, in the display 29, the speed of movement of the pushing element 30.

Figure 3:
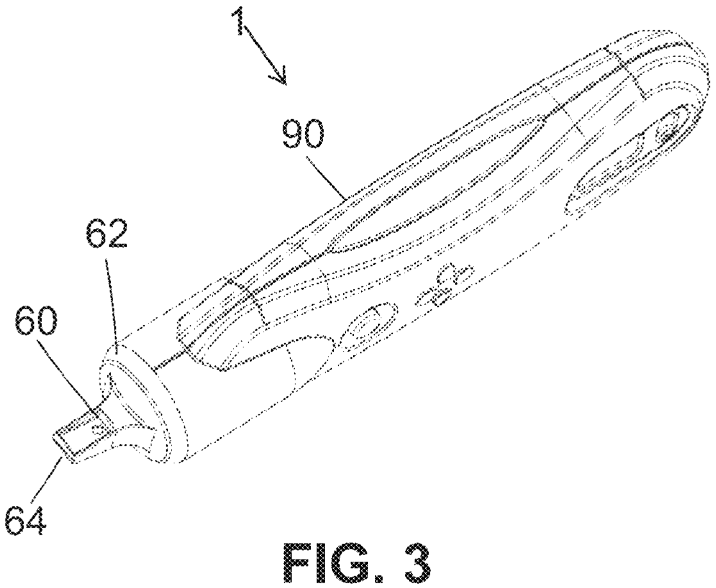
FIG. 3 schematically illustrate, according to an exemplary embodiment, a side perspective view of a wax applicator.

Referring now to FIG. 3, schematically illustrating, according to an exemplary embodiment, a side perspective view of a wax applicator. FIG. 3 particularly shows a wax application head 60 attached to the wax applicator 1. According to one embodiment, the wax applicator 1 further comprises at least one wax application head 60 configured to attach to an opening 102 that allows exit of melted wax from the wax chamber 10, and allow passage of the melted wax through the wax application head 60. According to one embodiment, the wax application head 60 is hollow, and comprises an attachment portion 62 at one side of the wax application head 60, configured to attach to the opening 102 that allows exit of melted wax from the wax chamber 10, and a nozzle 64 at an opposite side of the wax application head 60, configured to allow application of a controlled amount of the melted wax on the skin of the patient. Thus, when the wax application head 60 is attached to the opening 102 that allows exit of melted wax from the wax chamber 10, and when the melted wax is pushed out of the wax chamber 10 by the pushing element 30, the melted wax enters into the wax application head 60, passes through the wax application head 60, and exits through the nozzle 64.

According to one embodiment, the wax applicator 1 comprises a set of multiple wax application heads 60. The attachment portion 62 of the wax application heads 60 is similar in all the wax application heads 60, in order to allow attachment of all the wax application heads to the opening 102 that allows exit of melted wax from the wax chamber 10. On the other hand, the size and shape of the nozzle 64 of the wax application heads 60 is different in each wax application head 60. This allows a user to apply the melted wax on the skin of the patient in various amounts and textures of the applied melted wax, as well as to adjust the amount and texture of the applied melted wax to the area of the skin on which the melted wax is applied, simply by changing the wax application head 60 that is attached to the opening 102. For example, a wide and big nozzle 64 allows application of a large amount of melted wax over a wide area of the skin, while a narrow and small nozzle 64 allows application of a small amount of melted wax over a narrow area of the skin.

Figure 4B:
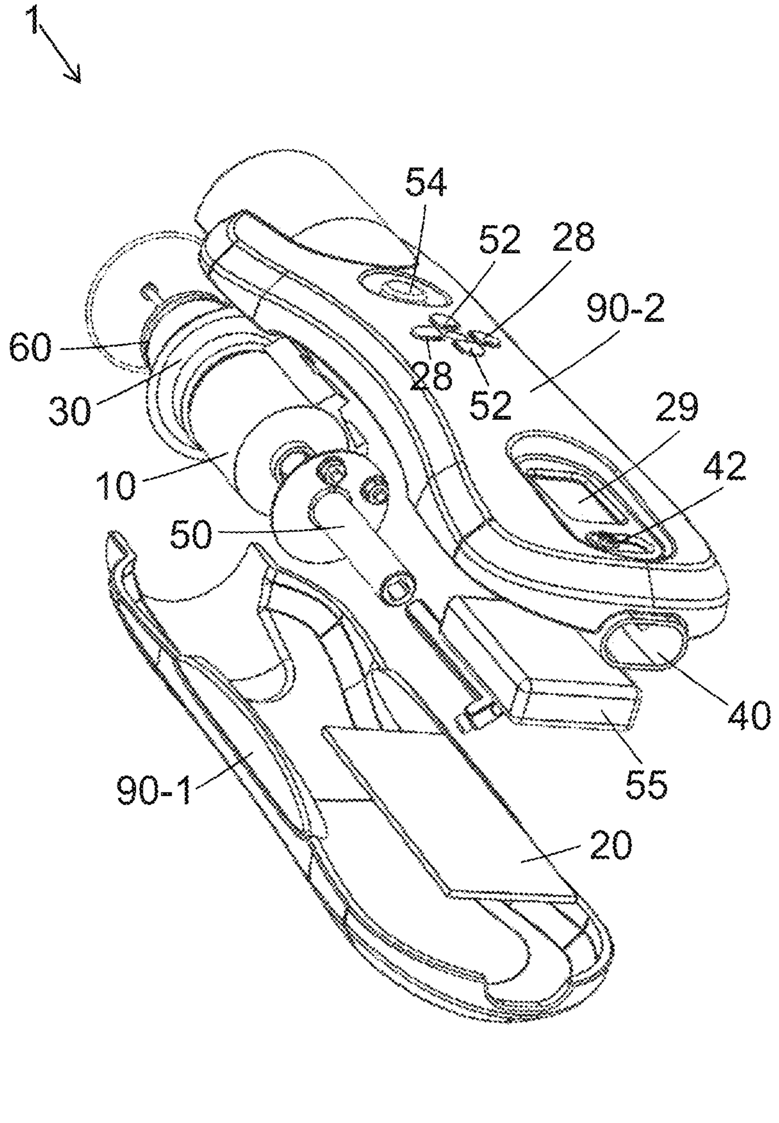
Figure 4C:
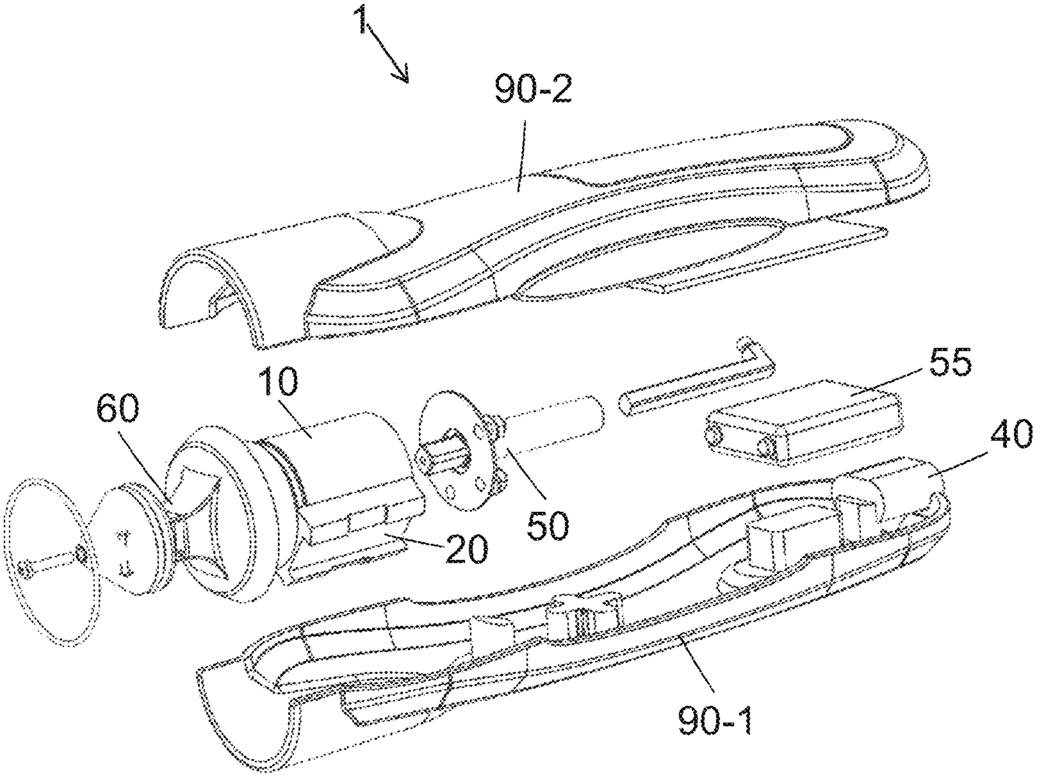

Referring now to FIGS. 4A-C, schematically illustrating, according to an exemplary embodiment, various different aspects of an exploded view of a wax applicator. FIGS. 4A-C show components of the wax applicator 1 mentioned above, for example, the wax chamber 10, the heating element 20, the temperature setting switch 28, the display 29, the pushing element 30, the electrical socket 40, the on-off switch 42, the motor 50, the direction switch 52, and the speed switch 54. In addition, as can be seen in FIGS. 2 and 3, the wax applicator 1 further comprises a body 90 configured to enclose internal components of the wax applicator 1, like the wax chamber 10, the heating element 20, the pushing element 30, and the motor 50; and carry on an external surface of the body 90 external components of the wax applicator 1, like the temperature setting switch 28, the display 29, the electrical socket 40, the on-off switch 42, the direction switch 52, and the speed switch 54. Any type and any configuration of the body 90 is under the scope of the present subject matter. According to the exemplary embodiment shown in FIGS. 4A-C, the body 90 comprises a first body part 90-1 and a second body part 90-2 that are configured to attach one to the other and enclose the internal parts of the wax applicator 1, while the external surface of at least one of the first body part 90-1 and the second body part 90-2 is configured to carry the external components of the wax applicator 1.

Figure 5A:
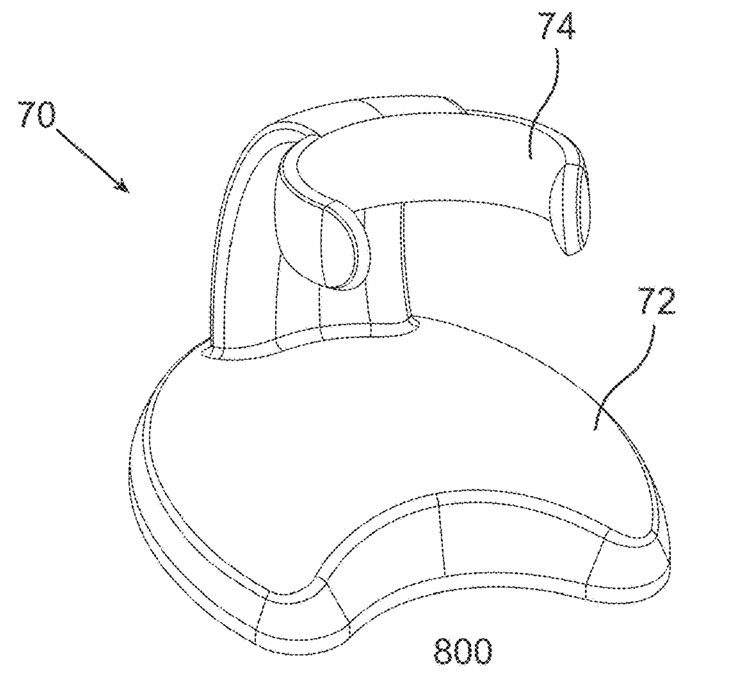
FIGS. 5A-B schematically illustrate, according to an exemplary embodiment, a stand and a wax applicator held by the stand, respectively.
Figure 5B:
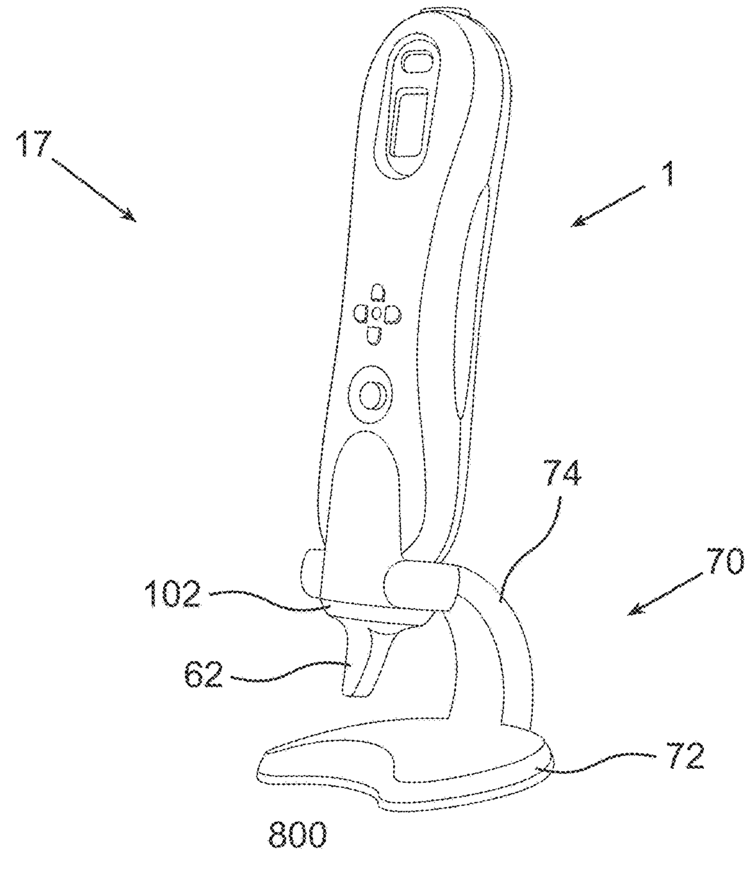

Referring now to FIGS. 5A-B, schematically illustrating, according to an exemplary embodiment, a stand and a wax applicator held by the stand, respectively. Thus, according to one embodiment, the wax applicator 1 further comprises a stand 70 configured to hold the wax applicator 1. FIG. 5A shows the stand 70, that comprises a base 72 configured to stand on or attach to a surface 800, and a holding element 74 attached to the base 72 and configured to hold the wax applicator 1. According to one embodiment, the base 72 is configured to stand on a horizontal surface 800, for example a table, a shelf, and the like. According to another embodiment, the base 72 is configured to attach to a diagonal or vertical surface, for example a diagonal wall, a vertical wall, and the like. The holding element 74 is configured to hold the wax applicator 1. Thus, when the wax applicator 1 is not in use it can be held by the holding element 74 of the stand 70 as shown in FIG. 5B. According to one embodiment, the stand 70 is configured to hold the wax applicator 1 in a manner that the opening 102 that allows exit of melted wax from the wax chamber 10 faces downwards. When the wax application head 60 is attached to the opening 102, the stand 70 is configured to hold the wax applicator 1 in a manner that the application head faces downwards, as shown in FIG. 5B. According to another embodiment, the stand 70 is configured to diagonally hold the applicator 1, an angle relative to the surface 800, as shown in FIG. 5B. It should be noted, though, that these embodiments are only exemplary and should not be considered as limiting the scope of the present subject matter. The stand 70 can be configured to hold the wax applicator 1 in any orientation.

According to one embodiment, the stand 70 is a charging stand 70 that is configured to electrically charge a rechargeable power source 45 of the wax applicator 1. Any mechanism for charging the rechargeable electrical power source 45, through the stand 70, but also without the stand 70, is under the scope of the present subject matter, for example wireless charging, charging through an electrical cable, and a like.

It is appreciated that certain features of the subject matter, which are, for clarity, described in the context of separate embodiments, may also be provided in combination in a single embodiment. Conversely, various features of the subject matter, which are, for brevity, described in the context of a single embodiment, may also be provided separately or in any suitable sub combination.

Although the subject matter has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A system to apply heated wax onto a skin of a patient for hair removal comprising:

a wax applicator comprising:

a wax chamber having at least one opening;

a heating element attached to the wax chamber, configured to heat the wax in the wax chamber, thus giving rise to melted wax;

a thermostat and a temperature sensor configured to sense a temperature of the wax in the wax chamber, wherein the thermostat is electrically connected to the heating element, and the temperature sensor is signally connected to the thermostat, wherein the temperature sensor is configured to sense the temperature of the wax that is in the wax chamber and transmit a signal indicative of the sensed temperature to the thermostat, and wherein the thermostat is configured to compare between the sensed temperature and a predetermined threshold temperature and accordingly switch-on or switch-off the heating element, and a pushing element configured to push the melted wax out of the wax chamber through at least one of the at least one opening, wherein at least one component of the wax applicator is an electrically operated component, and the electrically operated component is electrically connected to an electrical power supply.

2. The wax applicator of claim 1, wherein the electrical power supply is electricity mains, and the wax applicator further comprising an electrical socket electrically connected to the electrically operated component, and is configured to electrically connect to the electricity mains.

3. The wax applicator of claim 1, wherein the heating element is an electrical heating element.

4. The wax applicator of claim 1, further comprising an on-off switch electrically connected between the electrical power supply and the electrically operated component.

5. The wax applicator of claim 1, further comprising at least one temperature setting switch electrically connected to the thermostat and configured to allow determination of the threshold temperature.

6. The wax applicator of claim 1, further comprising at least one display configured to display parameters indicative of operation of the wax applicator.

7. The wax applicator of claim 1, wherein the pushing element is a piston like pushing element configured to be pushed inside the wax chamber, thereby push melted wax from the wax chamber through the at least one opening.

8. The wax applicator of claim 1, further comprising an electrical motor mechanically attached to the pushing element, and configured to actuate the pushing element.

9. The wax applicator of claim 8, further comprising a screwed shaft positioned between the motor and the pushing element, wherein the motor is configured to turn the screwed shaft in two directions—clockwise and counterclockwise, wherein when he screwed shaft is turned in one direction the screwed shaft is pushed forward and thereby push the pushing element in the wax chamber toward an opening that allows exit of melted wax from the wax chamber, and wherein when the screwed shaft is turned in an opposite direction the screwed shaft is pulled backward and thereby pull the pushing element in the wax chamber away from the opening that allows exit of melted wax from the wax chamber.

10. The wax applicator of claim 8, further comprising at least one direction switch configured to control the direction of turning of the motor, thereby controlling a direction of movement of the pushing element.

11. The wax applicator of claim 8, further comprising at least one speed switch configured to control a speed of turning of the motor, thereby control a speed of movement of the pushing element.

12. The wax applicator of claim 1, further comprising at least one wax application head configured to attach to an opening that allows exit of melted wax from the wax chamber, and allow passage of the melted wax through the wax application head.

13. The wax applicator of claim 12, wherein the wax application head is hollow, and comprising an attachment portion at one side of the wax application head, configured to attach to the opening that allows exit of melted wax from the wax chamber, and a nozzle at an opposite side of the wax application head, configured to allow application of a controlled amount of the melted wax on the skin of the patient.

14. The wax applicator of claim 13, comprising a set of multiple wax application heads, wherein the attachment portion is similar in all the wax application heads, and a size and shape of the nozzle is different in each wax application head.

15. The wax applicator of claim 1, further comprising a body including:

a first body part and a second body part that are configured to attach one to the other and enclose internal parts of the wax applicator, while an external surface of at least one of the first body part and the second body part is configured to carry external components of the wax applicator.

16. The wax applicator of claim 1, further comprising a stand configured to hold the wax applicator, wherein the stand comprising: a base configured to stand on or attach to a surface; and a holding element attached to the base and configured to hold the wax applicator.

17. The wax applicator of claim 16, wherein the at least one opening allows exit of melted wax from the wax chamber and the stand is configured to hold the wax applicator in a manner that the at least one opening faces downwards.

18. The wax applicator of claim 17, wherein the stand is configured to diagonally hold the applicator at an angle relative to horizontal.

19. A method of applying heated wax onto a skin of a patient for hair removal, the method comprising:

providing a wax applicator configured to apply heated wax onto a skin of a patient for hair removal, the wax applicator comprising: a wax chamber having at least one opening;

a heating element attached to the wax chamber, configured to heat the wax in the wax chamber, thus giving rise to melted wax; and a pushing element configured to push the melted wax out of the wax chamber through at least one of the at least one opening, wherein at least one component of the wax applicator is an electrically operated component, and the electrically operated component is electrically connected to at least one electrical power supply;

sensing a temperature of the wax in the wax chamber by a thermostat and a temperature sensor configured to sense, wherein the thermostat is electrically connected to the heating element, and the temperature sensor is signally connected to the thermostat, wherein the temperature sensor is configured to sense the temperature of the wax that is in the wax chamber and transmit a signal indicative of the sensed temperature to the thermostat, and wherein the thermostat is configured to compare between the sensed temperature and a predetermined threshold temperature and according switch-on or switch-off the heating element;

filling the wax chamber with the wax; melting the wax by heating; and pushing the melted wax out from the wax chamber while applying the melted wax on the skin of the patient.

* * * * *